ively active enantiomeric form,
United States Patent
Lohmann et al.

[11] Patent Number: 4,997,966
[45] Date of Patent: Mar. 5, 1991

[54] ENANTIOMERIC SILANES, MODIFIED PACKING MATERIAL, AND USE THEREOF

[75] Inventors: Dieter Lohmann; Richard Däppen, both of Münchenstein, Switzerland

[73] Assignee: Ciba-Geigy Corporation, Ardsley, N.Y.

[21] Appl. No.: 447,276

[22] Filed: Dec. 7, 1989

[30] Foreign Application Priority Data

Dec. 20, 1988 [CH] Switzerland ............ 4761/88

[51] Int. Cl.$^5$ .................... C07F 7/10; C07F 7/08; C07F 7/18
[52] U.S. Cl. .................... 556/420; 556/415
[58] Field of Search .................... 556/420, 415

[56] References Cited

U.S. PATENT DOCUMENTS

| 4,812,512 | 3/1989 | Buendia et al. | 556/420 X |
| 4,824,950 | 4/1989 | Barcza | 556/420 X |
| 4,861,908 | 8/1989 | Satoh et al. | 556/420 |

FOREIGN PATENT DOCUMENTS 0935740 9/1963 United Kingdom ........... 556/420 X

Primary Examiner—Paul F. Shaver
Attorney, Agent, or Firm—Stephen V. O'Brien

[57] ABSTRACT

A compound of formula I

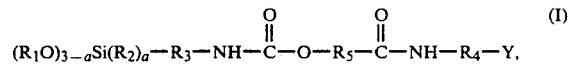

wherein
$R_1$ is $C_1$-$C_4$alkyl, phenyl or benzyl,
$R_2$ is $C_1$-$C_4$alkyl, phenyl or benzyl,
a is 0, 1 or 2,
$R_3$ is linear or branched unsubstituted or OH-substituted $C_1$-$C_{12}$alkylene or is phenylene,
$R_5$ is the divalent radical, diminished by the —CO—O group, of a lactone having a total of 4 to 7 ring members and containing at least one chiral carbon atom and corresponding predominantly to an optically active enantiomeric form,
$R_4$ is a direct bond, $C_1$-$C_4$alkyl—CH or $CF_3$—CH, and
Y is phenyl, naphthyl, fluorenyl or anthryl, each unsubstituted or substituted by $C_1$-$C_{12}$alkyl, $C_1$-$C_{12}$alkoxy, halogen, —CN or —$NO_2$.

These compounds are suitable for the preparation of stationary phases for the chromatographic separation of chiral compounds.

18 Claims, No Drawings

ENANTIOMERIC SILANES, MODIFIED PACKING MATERIAL, AND USE THEREOF

The present invention relates to enantiomers of isocyanate-functional organosilanes and chiral hydroxycarboxamides, to a packing material modified with these enantiomers as stationary phase for chromatographic separation methods, and to the use of said packing material for the chromatographic separation of, in particular, chiral compounds.

It is known that chiral substances have different effects on an organism. The provision of chiral substances as reagents or intermediates for the preparation of chiral compounds has become of great importance. Besides the stereospecific synthesis of such compounds, chromatographic methods in particular are used for the separation of enantiomers. Mainly stationary phases are used for this purpose, a number of which are commercially available. Such stationary phases may be, for example, solid packing materials which are modified with chiral substances. It is also possible to use natural and synthetic polymers which contain chiral structural units. Silica gel, the OH groups of which may be chemically derivatised at the surface, can typically be used as solid packing material. Solid polymers containing functional groups which can be derivatised may also be suitably used. For the chiral differentiation of racemates, the packing materials can be derivatised, for example, with chiral compounds (q.v. R. Däppen et al., Journal of Chromatography, 373, pp, 1–20 (1986).

Reaction products of (aminoalkyl)alkoxysilanes with achiral lactones which may be used, for example, as couplers in glass-reinforced plastics are disclosed in U.S. Pat. No. 4,104,296. In J. Org. Chem., Vol. 51, pp. 1641–1644, (1986), J. F. W. Keana at al. report on the use of silica gel modified with racemic N-[3-triethoxysilyl)propyl]-10-trichloro-10-hydroxy-10-methylundecanamide for solid phase syntheses.

In Tetrahedron Letters 26, No. 35, pp. 4217–4220 (1985), Y. Dobashi et al. describe tartramide group containing solid phases for the chromatographic separation of enantiomers. European patent application No. 0 105 745 discloses optically active isocyanates which are reacted with amino-functional silica gels to give chirally modified solid phases for the chromatographic separation of enantiomers.

In one of its aspects, the present invention relates to compounds of formula I $$(R_1O)_{3-a}Si(R_2)_a-R_3-NH-\overset{O}{\underset{\|}{C}}-O-R_5-\overset{O}{\underset{\|}{C}}-NH-R_4-Y, \quad (I)$$

wherein
$R_1$ is $C_1$–$C_4$alkyl, phenyl or benzyl,
$R_2$ is $C_1$–$C_4$alkyl, phenyl or benzyl,
a is 0, 1 or 2,
$R_3$ is linear or branched unsubstituted or OH-substituted $C_1$–$C_{12}$alkylene or is phenylene,
$R_5$ is the divalent radical, diminished by the —CO—O group, of a lactone having a total of 4 to 7 ring members and containing at least one chiral carbon atom and corresponding predominantly to an optically active enantiomeric form,
$R_4$ is a direct bond,

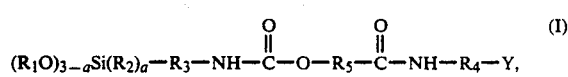

Y is phenyl, naphthyl, fluorenyl or anthryl, each unsubstituted or substituted by $C_1$–$C_{12}$alkyl, $C_1$–$C_{12}$alkoxy, halogen, —CN or —NO$_2$.

$R_1$ as alkyl may be linear or branched and is typically methyl, ethyl, n-propyl and isopropyl, n-butyl, isobutyl or tert-butyl. The preferred meaning of $R_1$ is methyl or ethyl.

$R_2$ as alkyl may be linear or branched and is typically methyl, ethyl, n-propyl and isopropyl, n-butyl, isobutyl or tert-butyl. The preferred meaning of $R_2$ is methyl.

In formula I, a is preferably 0 or 1 and, most preferably, is 0.

$R_3$ as alkylene preferably contains 1 to 6, most preferably 3 or 4, carbon atoms, and is unsubstituted or substituted by hydroxyl. Illustrative of alkylene are methylene, 1,1- or 1,2-ethylene, 1,1-, 1,2- or 1,3-propylene, 1,2-, 1,3- or 1,4-butylene, 2-methyl-1,3-propylene, 1,2-, 1,3-, 1,4- or 1,5-pentylene, 1,2-, 1,3-, 1,4-, 1,5- or 1,6-hexylene, heptylene, octylene, nonylene, decylene, undecylene or dodecylene.

$R_3$ as phenylene is preferably 1,3- or 1,4-phenylene.

More particularly $R_3$ is —(CH$_2$)$_n$—, —CH(CH$_3$)— or —CH$_2$—CH(CH$_3$)—CH$_2$-, where n is preferably 3 or 4. Most preferably, $R_3$ is 1,3-propylene.

$R_4$ may be $C_1$–$C_4$alkylmethylidene, wherein alkyl is typically methyl, ethyl, n-propyl or isopropyl, or n-butyl, isobutyl or tert-butyl. Alkyl is most preferably methyl. In a preferred embodiment of the invention, $R_4$ is ethylidene, 1,1-propylidene or 1,1,1-trifluoroethylidene.

Y may carry one or more substituents, preferably one to three and, most preferably, one or two substituents. Alkyl and alkoxy substituents contain preferably 1 to 6, most preferably 1 to 4, carbon atoms. Illustrative are methyl, ethyl, n-propyl and isopropyl, n-butyl, isobutyl and tert-butyl, and corresponding alkoxy groups. Halogen is preferably —F, —Cl and —Br. Preferred substituents of Y are $C_1$–$C_4$alkyl, $C_1$–$C_4$alkoxy, —F, —Cl, —Br, —CN and —NO$_2$.

A preferred embodiment of the invention is that wherein Y is phenyl or naphthyl, each unsubstituted or substituted by $C_1$–$C_4$alkyl, $C_1$–$C_4$alkoxy, —F, —Cl, —Br, —CN or —NO$_2$. Another preferred embodiment is that wherein $R_4$ is a direct bond and Y is 3,5-dinitrophen-1-yl or 3,5-dicyanophen-1-yl.

Particularly preferred compounds of formula I are those wherein $R_4$ is ethylidene and Y is naphthyl or substituted naphthyl. Still more preferred compounds of formula I are those wherein —$R_4$—Y is the (R)- or (S)-form of

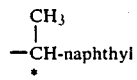

Where $R_5$ is the divalent radical of a lactone, said lactone preferably contains 4 to 6, most preferably 4 or 5, ring members. Depending on the size of the ring, the lactone may contain 1 to 6, preferably 1 to 4 and, most preferably, 1 or 2, chiral carbon atoms. A chiral carbon atom in the radical $R_5$ is preferably α- or β-orientated to the OH group. The expression "predominantly optically active enantiomeric form" means, for example, not less than 90%, preferably not less than 95%, of an optically active enantiomeric form. The pure optically active enantiomeric form is preferred.

The lactones from which the divalent radical $R_5$ is derived may be, for example, at least monosubstituted lactones of saturated $C_3$–$C_6$hydroxycarboxylic acids or ethylenically unsaturated $C_4$–$C_6$hydroxycarboxylic acids, or may be hydroxycarboxylic acids of formula VII

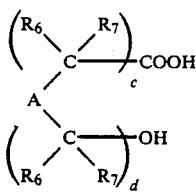
(VII)

wherein c and d are each 0 or 1 and one of c or d is 1, $R_6$ and $R_7$ are H, $C_1$–$C_6$alkyl, —$CF_3$, or phenyl or naphthyl or substituted phenyl or naphthyl, and A is a monocyclic or polycyclic saturated or ethylenically unsaturated cycloaliphatic or heterocyclic-aliphatic radical of 4 to 18, preferably 5 to 12, carbon atoms and containing preferably O, S or N as hetero atoms, or A is $C_6$–$C_{16}$arylene in 1,2-position or $C_5$–$C_{16}$heteroarylene containing preferably O, S or N as hetero atom, with the proviso that at least one of c or d is 1 and $R_6$ and $R_7$ are different from each other.

These lactones or the radical A in formula VII from which $R_5$ is derived may be unsubstituted or substituted by $C_1$–$C_6$alkyl, $C_1$–$C_6$alkoxy, $C_1$–$C_6$alkylthio, $C_1$–$C_{12}$alkylamino, $C_5$ or $C_6$cycloalkyl, $C_5$ or $C_6$cycloalkoxy, $C_6$–$C_{10}$aryl, $C_6$–$C_{10}$aryloxy, $C_7$–$C_{11}$aralkyl, $C_7$–$C_{12}$aralkoxy, $C_1$–$C_6$haloalkyl, $C_1$–$C_6$hydroxyalkyl, $C_1$–$C_6$alkoxymethyl, ($C_6$–$C_{12}$aryloxy)methyl, ($C_6$–$C_{18}$aryl)methoxymethyl, $C_1$–$C_{12}$acyloxy, —CO—$R_8$, —F, —Cl, —Br, —OH or —CN, where $R_8$ is $C_1$–$C_6$alkyl, cyclohexyl, phenyl or benzyl. Typical substituents are methyl, ethyl, n-propyl, isopropyl, n-butyl, isobutyl and tert-butyl, pentyl, hexyl and corresponding oxy and thio radicals; cyclopentyl, cyclohexyl and corresponding oxy and thio radicals; phenyl, phenoxy, phenylthio; benzyl, triphenylmethoxy, benzyloxy, benzylthio, fluoromethyl, trifluoromethyl, chloromethyl, trichloromethyl, β-chloroethyl; hydroxymethyl, β-hydroxyethyl; methoxymethyl, ethoxymethyl, β-methoxyethyl; phenoxymethyl, naphthoxymethyl; benzyloxymethyl, (diphenylmethoxy)methyl, (triphenylmethoxy)methyl; formyloxy, acetoxy, n-propionyloxy and isopropionyloxy, n-butyroyloxy, isobutyroyloxy and tert-butyroyloxy; methoxycarbonyl, ethoxycarbonyl; —F, —Cl, —Br, —OH and —CN.

Illustrative of divalent radicals of hydroxycarboxylic acid are 1,2-propylene, 3-chloro-1,2-propylene, 3,3-dichloro-1,2-propylene, 3,3,3-trichloro-1,2-propylene, 3,3,3-trichloro-2-methyl-1,2-propylene, 4,4,4-trichloro-1,3-butylene, but-1-enyl-1,3-ene, 2-methylbut-1-enyl-1,4-ene, 1,2,3,4-tetrahydroxybutyl-1,4-ene, 1,2,3,4,5-pentahydroxypentyl-1,5-ene, 2-methyl-1,3-propylene, 2,2-dimethyl-3-hydroxy-1,3-propylene, 1-hydroxy-1,3-propylene, 1-(ethoxycarbonyl)-1,3-propylene, 1-(triphenylmethoxy)-1,3-propane, 3-(α,β-dihydroxyethyl)-1,2-dihydroxy-1,3-propylene.

The cyclic non-aromatic radicals A in formula VII may be in 1,2-, 1,3- or 1,4-position. Illustrative of radicals A are 1,2-cyclobutylene, 1,2-cyclopentylene, 1,2-cyclohexylene, 2,3-tetrahydrofuranylene, cyclohex-4-enyl-1,2-ene, 1,2-phenylene, 4-nitro-1,2-phenylene, 3,5-dinitro-1,2-phenylene, 2,3-naphthylene, 7-nitro-2,3-naphthylene, 2,3-pyridinylene, 2,3-furanylene, 2,3-pyrrolydene.

$R_6$ is preferably H. $R_6$ and $R_7$ as alkyl may be typically methyl, ethyl, n-propyl or isopropyl, n-butyl, isobutyl or tert-butyl, pentyl, hexyl, and are preferably methyl or ethyl.

Preferred compounds of formula I are those wherein $R_5$ is linear $C_2$–$C_5$alkylene or $C_3$–$C_5$alkenylene each of which is substituted by $C_1$–$C_6$alkyl, $C_1$–$C_6$alkoxy, $C_1$–$C_6$alkylthio, $C_1$–$C_{12}$alkylamino, $C_5$ or $C_6$cycloalkyl, $C_5$ or $C_6$cycloalkoxy, $C_6$–$C_{10}$aryl, $C_6$–$C_{10}$aryloxy, $C_7$–$C_{11}$aralkyl, $C_7$–$C_{12}$aralkoxy, $C_1$–$C_6$haloalkyl, $C_1$–$C_6$hydroxyalkyl, $C_1$–$C_6$alkoxymethyl, ($C_6$–$C_{12}$aryloxy)methyl, ($C_6$–$C_{18}$aryl)methoxymethyl, $C_1$–$C_{12}$acyloxy, —CO—$R_8$, —F, —Cl, —Br, —OH or —CN, where $R_8$ is $C_1$–$C_6$alkyl, cyclohexyl, phenyl or benzyl.

Preferred substituents are $C_1$–$C_4$alkyl, $C_1$$C_1$–$C_4$alkoxy, $C_1$–$C_6$alkylamino, $C_5$ or $C_6$cycloalkyl, $C_5$ or $C_6$cycloalkoxy, phenyl, naphthyl, phenoxy, benzyl, benzyloxy, diphenylmethoxy, trityloxy, $C_1$–$C_4$haloalkyl, preferably trichloromethyl, $C_1$–$C_6$hydroxyalkyl, $C_1$–$C_4$alkoxymethyl, phenoxymethyl, benzyloxymethyl, $C_2$–$C_8$acyloxy, —CO—$OR_8$, —F, —Cl, —Br, —OH, and —CN, where $R_8$ is $C_1$–$C_4$alkyl, cyclohexyl, phenyl or benzyl.

Another preferred embodiment of this invention relates to compounds of formula I, wherein $R_5$ is a radical of formula II

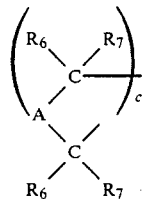
(II)

wherein
A is 1,2-phenylene or 2,3-naphthylene, each unsubstituted or substituted by —F, —Cl, —Br, —OH, —CN, —$NO_2$, $C_1$–$C_6$alkyl or $C_1$–$C_6$alkoxy, c is 0 or 1, and $R_6$ and $R_7$ are different from each other and are H, $C_1$–$C_6$alkyl, —$CF_3$, unsubstituted phenyl or naphthyl, or phenyl or naphthyl each substituted by —F, —Cl, —Br, —OH, —CN, —$NO_2$, —$CF_3$, $C_1$–$C_6$alkyl or $C_1$–$C_6$alkoxy. Preferred substituents of A are —F, —Cl, —Br, —CN, —$NO_2$, $C_1$–$C_4$alkyl and $C_1$–$C_4$alkoxy.

$R_6$ and $R_7$ are preferably H, $C_1$–$C_4$alkyl, —$CF_3$, phenyl or naphthyl. Preferred substituents of phenyl or naphthyl are —F, —Cl, —Br, —CN, —$NO_2$, —$CF_3$, $C_1$–$C_4$alkyl or $C_1$–$C_4$alkoxy.

In a preferred embodiment of the invention, $R_5$ is the divalent radical of a β-lactone which is diminished by the —COO group and which preferably contains one chiral carbon atom.

In a particularly preferred embodiment of the invention, $R_5$ is the R- or S-form of

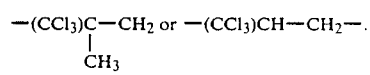

Most preferably, the compounds of formula I are the stereoisomers of formula

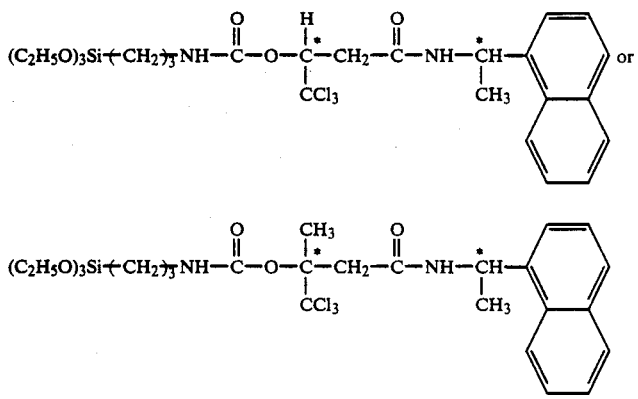 or wherein * denotes the chiral carbon atom in R- or S-form. In the above formulae, the left C* denotes preferably the R-form and the right C* preferably the S-form.

The invention further relates to a process for the preparation of compounds of formula I, which comprises reacting a compound of formula III

  (III)

with a compound of formula IV

  (IV)

in which formulae above $R_1$, $R_2$, $R_3$, $R_4$, $R_5$, Y and a have the meanings previously assigned to them.

The method is known per se. Equimolar amounts of the compounds of formulae III and IV will normally be used. The reaction may, for example, be carried out by adding a solution of the compound of formula III, preferably at room temperature, to a solution of the compound of formula IV. Working up can be effected by conventional methods, for example by evaporating off the solvent and purifying the distillation residue, for example by distillation, recrystallisation or chromatographic methods. It is useful to speed up the reaction catalytically with amines, diaza compounds or organotin compounds, for example diazabicyclooctane, pyridine or dibutyltin dilaurate.

Illustrative of suitable solvents are aprotic solvents such as ethers (diethyl ether, tetrahydrofuran, dioxane), halogenated aliphatic hydrocarbons (methylene chloride, chloroform), and hydrocarbons (hexane, cyclohexane, toluene).

The compounds of formula IV can be obtained in simple manner by reacting a lactone of formula VII

  (VII)

with an amine of formula Y—$R_4$—$NH_2$ (VIII).

The compounds of formula III and VIII are known, are obtainable by known methods or are commercially available. Very numerous optically active lactones of formula VII are known or can be prepared by known methods (q.v. for example J. Chem. Soc., Vol. 104, pp. 166–168 (1982), J. Org. Chem., 52, pp. 3011–3017 (1987), J. Chromatogr., 387, pp. 313–323 (1987), Houben-Weyl 6/2, pp. 515–527 (1963), Houben-Weyl 6/2, p. 571 et seq., (1963), Houben-Weyl E 5/1, pp. 715–773 (1985), Georg Thieme Verlag, Stuttgart/New York). Racemates can be separated by known methods.

The compounds of formula I are suitable, for example, for the preparation of packing materials for chromatographic separation methods.

In another of its aspects, the present invention also relates to a packing material wherein radicals of formulae Va, Vb and/or Vc

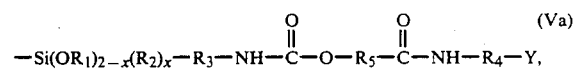  (Va)

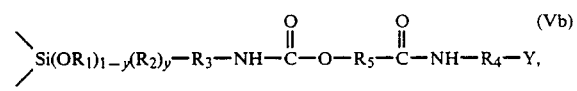  (Vb)

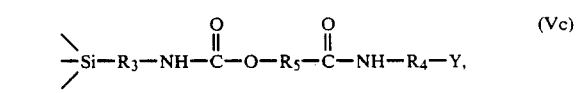  (Vc)

wherein x is 0, 1 or 2 and y is 0 or 1, and $R_1$, $R_2$, $R_3$, $R_4$, $R_5$ and Y have the meanings previously assigned to them, are attached to a linking group of a solid support. The preferred meanings of $R_1$, $R_2$, $R_3$, $R_4$, $R_5$ and Y are also as previously stated. The linking group is preferably —O—.

In yet another of its aspects, the present invention relates to a process for the preparation of a packing material, which comprises reacting (a) a solid packing material which contains radicals of formulae VIa, VIb and/or VIc

  (VIa),

  (VIb)

  (VIc)

attached through linking groups, with a compound of formula IV

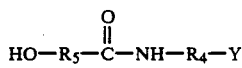

or (b) reacting a solid packing material which contains groups which are reactive to the silane group $(R_1O)_{3-a}Si(R_2)_a$—, with a compound of formula I, wherein x is 0, 1 or 2, and y is 0 or 1, and $R_1$, $R_2$, $R_3$, $R_4$, $R_5$ and Y have the meanings previously assigned to them.

The preferred meanings of $R_1$, $R_2$, $R_3$, $R_4$, $R_5$ and Y are also as previously stated. The reactive groups are preferably OH groups.

The solid packing materials may be typically glass, silicates, silica gel, $Al_2O_3$ or $TiO_2$. The packing material is preferably in the form of fine particles. Such packing materials are widely described in the literature [q.v. M Verzele et al., Preparative High Performance Liquid Chromatography, Drukkerig De Muyter, Belgium, pp. 77-89 (1986); R. W. Souter, Chromatographic Separations of Stereoisomers, CRC Press, pp. 117-195 (1985), W. Noll, Chemie und Technologie der Silicone, Verlag Chemie, Weinheim (1968), Laborbücher Chemie, Praxis der Hochleistungs-Flüssigchromatographie, Verlag Moritz Diesterweg, pp. 76-78 (1986)]. A particularly preferred packing material is silica gel.

Some of the packing materials suitable for use in process variant (a) are commercially available or they can be prepared by known methods. Process variant (b) is preferred.

The process can be performed by carrying out the reaction in a separate reactor, and then packing a chromatography column with the reaction product. However, it is also possible to perform the process by carrying the reaction, for example, in a chromatography column or with coated thin-layer plates which are filled or coated with a packing material according to process variant (a) or (b). These processes are known per se. Process variant (b) is especially preferred.

The reaction may be carried out, for example, by suspending the packing material in an inert solvent, for example in a hydrocarbon such as hexane, benzene, toluene or xylene. To this suspension can then be added a solution of an enantiomeric compound of formula IV or a compound of formula I. The solvent used for preparing the suspension will conveniently be used as solvent. During the addition, the temperature will conveniently be kept at room temperature. The reaction mixture is then further stirred, preferably at elevated temperature, for example in the range from 50° to 150° C. The alcohol which forms is removed as an azeotrope. The reaction product can then either be packed into columns for chromatographic separations or the material is collected by filtration, washed, dried and stored for use. However, the solvent can also be removed before the further stirring, for example by distillation under normal pressure or under vacuum, and the dry residue heated for a time, under normal pressure or under vacuum, to a temperature in the range from 50° to 150° C., and subsequently washed and dried.

The packing material of this invention is excellently suitable for use as stationary phase for the chromatographic separation of chiral compounds, especially in liquid chromatography. The invention also relates to this utility.

The chromatographic packing material of this invention affords various advantages. The elution sequence can be influenced by the absolute configurations of the lactones. The packing material is suitable for separating racemates which are otherwise difficult to separate or which can only be separated after prior derivitisation, for example racemic diols, diamines, and rotation isomers. Besides enantiomers, it is also possible to separate diastereoisomers and other stereoisomers. The material has high chemical stability, thereby ensuring long use. The preparative capacity is high.

The solvents employed are normally hexane, lower alcohols or ethers or mixtures thereof. The packing material of this invention makes it possible to use technical solvents and strongly polar solvents, for example $CH_2Cl_2$, $CHCl_3$, acetone, ethyl acetate, tetrahydrofuran, dioxan or acetonitrile. The use of polar solvents makes it possible to shorten the elution times substantially—a feature which is important for preparative chromatography. Supercritical solvents can also be used, for example carbon dioxide.

The high enantioselectivities are particularly surprising when in the group —$R_5$—OH the chiral selector

is in terminal position, where R' is H or $C_1$-$C_6$alkyl such as methyl, ethyl, propyl or butyl.

The theoretical number of plates of the columns, as benchmark for assessing the quality of the packing, is determined in conventional manner with toluene as reference substance as described, for example, by V. Meyer, "Praxis der Hochleistungsflüssigchromatographie", 4th edition, Diesterweg/Salle/Sauerländer 1986, page 20, Frankfurt.

The characterisation of the columns is made in conventional manner as described, for example, by V. Meyer, "Praxis der Hochleistungsflüssigchromatographie", 4th edition, Diesterweg/Salle/Sauerländer 1986, page 18 et seq., Frankfurt, with the capacity factors $k_1$ and $k_2$ as well as the separation factor $\alpha$ and the resolution factor $R_s$.

The following Examples illustrate the invention in more detail.

(A) Preparation of the starting materials

Example 1

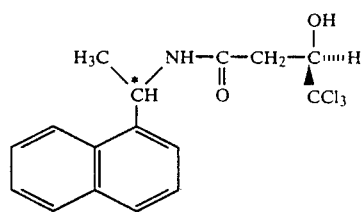

In a 25 ml round flask, a solution of 0.96 ml (5.277 mmol) of (±)-1-(naphthyl)ethylamine in 5 ml of dry toluene is added dropwise, in an atmosphere of dry nitrogen, to a solution of 1 g (5.277 mmol) of R-(−)-trichloromethyl-2-oxetanone. When the slightly exothermic reaction has subsided, the reaction mixture is stirred for 12 hours at room temperature. The clear solution so obtained is concentrated by evaporation and the residue is chromatographed over silica gel with toluene/ethyl acetate (9:1) as eluant, in which procedure the two diastereoisomers are separated and isolated as white crystalline substances.

diastereoisomer A: $[\alpha]_D^{20} = -18.9 \pm 1°$ (1.0%, CHCl$_3$). m.p. 149° C. Yield: 0.7 g (73.7 of theory).

diastereoisomer B: $[\alpha]_D^{20} = -52.4 \pm 1°$ (1.0%, CHCl$_3$). m.p. 54° C. Yield: 0.75 g (78.9 of theory).

Example 2

As described in Example 1, (a) enantiomeric S-(−)-1-(1-naphthyl)ethylamine and (b) enantiomeric R-(+)-1-(1-naphthyl)ethylamine are reacted with R-(−)-4-trichloromethyl-2-oxetanone. The comparison of the properties of the products so obtained with those of the diastereoisomers of Example 1 shows that diastereoisomer A has the absolute configuration S,R and diastereoisomer B the absolute configuration R,R.

Example 3

As described in Example 1, 2.5 g (0.01497 mol) of racemic 1-(1-naphthyl)ethylamine in 30 ml of toluene are reacted with 2.84 g (0.01497 mol) of racemic 4-trichloromethyl-2-oxetanone. The chromatographic separation of the isomers of the resultant product over silica gel with toluene/ethyl acetate (9:1) as eluant affords an initially eluted crystalline pair of enantiomers A: 2.5 g = 93.6% of theory, m.p. 171°–174° C.

and a later eluted crystalline pair of enantiomers B: 1.94 g = 72.6% of theory, m.p. 152°–154° C.

Example 4

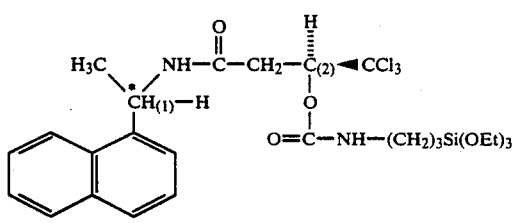

In a 100 ml three-necked flash fitted with stirrer, internal thermometer and gas inlet pipe, the diastereoisomer A prepared in accordance with Example 1 (4.5 g=0.01247 mol) is reacted, under an atmosphere of dry nitrogen, with 3-isocyanatopropyltriethoxysilane (3.1 g=0.125 mol) in toluene (100 ml), with the addition of diazabicyclooctane (20 mg) as catalyst. To bring the reaction to completion, the reaction mixture is heated for 3 hours to 50°–60° C., then concentrated by evaporation, and the residue is freed from solvent under a high vacuum. The crude product is purified by column chromatography over silica gel with n-hexane/diethyl ether (6:4) as eluant. The purity and the composition of the viscous colourless product are determined by thin-layer chromatography and elemental analysis.

Elemental analysis. Theory: C 51.36%; H 6.13%; N 4.60%; Cl 17.49%; Si 4.62%. Found: C 51.51%; H 6.37%; N 4.82%; Cl 17.06%; Si 4.87%.

Example 5

4 g of silica gel (Matrex Silica 5 μm 100 Å; Amicon Corp., Lausanne) are dried for 16 hours at 0.1 Pa and 150° C. To this silica gel is then added a solution of 1.5 g (2.6 mmol) of silane, prepared in accordance with Example 4, in 10 ml of dry toluene. The components are thoroughly mixed in a 50 ml bulb tube. The toluene is removed at 70° C./0.1 Pa. The dry powder is kept for 16 hours at 110° C. and 0.1 Pa. After cooling, the powder is washed on a G4 suction filter with 10 ml each of toluene, acetone and methanol, and dried overnight at 90° C./0.1 Pa to give 4.55 g of a pale beige powder containing 8.38% C, 1.48% H and 0.83% N, corresponding to a loading of 0.29 mmol/g of chiral silane (based on % age of C).

Example 6

0.81 g (2.2 mmol) of enantiomerically pure compound according to Example (2a) are dissolved in 10 ml of dry toluene. After addition of 0.49 g (0.20 mmol) of 3-isocyanopropyltriethoxysilane (Petrarch Systems, Bristol Pa), the mixture is stirred for 16 hours at 90° C. This mixture is added to 4.0 g of silica gel Matrex Silica 5 μm, 100 Å, Amicon Corp., Lausanne). The toluene is removed at 70° C./0.1 Pa. The dry powder is kept for 16 hours at 110° C. and 0.1 Pa. After cooling, the powder is washed on a G4 suction filter with 10 ml each of toluene, acetone and methanol, and dried overnight at 90° C./0.1 Pa to give 3.74 g of a pale beige powder containing 6.20% C, 1.30% H and 0.80% N, corresponding to a loading of 0.22 mmol/g of chiral silane (based on % age of C).

Example 7

An analytical HPLC column (d=0.46 cm; L=25 cm) is packed with 3.0 g of the material according to Example 5 as a dispersion in isopropanol with methanol at 600 bar at a rate of 5 ml/min. The quality test of the packed column using toluene as reference substance gives a theoretical number of plates of 13 000.

Example 8

An analytical HPLC column is packed with 3.0 g of the material according to Example 6 as described in Example 7. The theoretical number of plates is 12 500.

Example 9

1.0 g of Aerosil 380 (Degussa, Frankfurt) is reacted in accordance with Example 6. The cooled product is suspended in ethanol and decanted. The product is dried to give 0.5 g of a pale beige powder containing 13.2% C, 1.71% H and 1.55% N, corresponding to a loading of 0.46 mmol/g of chiral silane (based on % age of C). The specific surface area (BET) is 184 m$^2$/g.

(B) Use Examples

Example 10

The racemic compounds

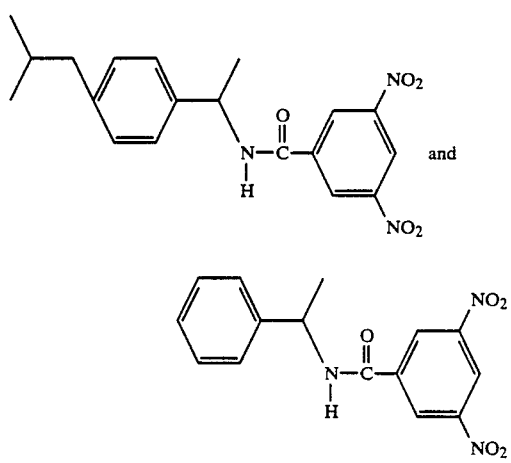

are separated into the enantiomers on columns according to Examples 7 and 8 using different eluants. The results are reported in the following Table.

| Column according to Example | Compound | Eluant | Pressure | $k_1'$ | $k_2'$ | $\alpha$ | $R_s$ |
|---|---|---|---|---|---|---|---|
| 7 | I | i-propanol/hexane (1:4) | 95/2 | 1.64 | 4.39 | 2.67 | 11.2 |
| 7 | I | i-propanol/hexane (2:3) | 104/2 | 0.53 | 1.40 | 2.64 | 9.20 |
| 7 | I | $CH_2Cl_2$ | 87/2 | 0.57 | 1.21 | 2.13 | 6.74 |
| 7 | I | $CHCl_3$ | 111/2 | 0.72 | 1.71 | 2.35 | 5.98 |
| 7 | I | t-butanol | 70/2 | 2.24 | 4.73 | 2.11 | 8.97 |
| 8 | I | i-propanol/hexane (1:4) | 97/2 | 1.01 | 2.30 | 2.28 | 9.35 |
| 7 | II | i-propanol/hexane (1:4) | 95/2 | 4.35 | 9.55 | 2.20 | 8.77 |
| 8 | II | i-propanol/hexane (1:4) | 95/2 | 2.50 | 5.33 | 2.13 | 11.14 |

What is claimed is:

1. A compound of formula I

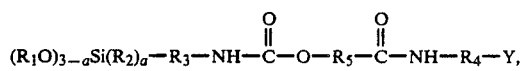

wherein
$R_1$ is $C_1$-$C_4$alkyl, phenyl or benzyl,
$R_2$ is $C_1$-$C_4$alkyl, phenyl or benzyl,
a is 0, 1 or 2,
$R_3$ is linear or branched unsubstituted or OH-substituted $C_1$-$C_{12}$alkylene or is phenylene,
$R_5$ is the divalent radical, diminished by the —CO—O group, of a lactone having a total of 4 to 7 ring members and containing at least one chiral carbon atom and corresponding predominantly to an optically active enantiomeric form,
$R_4$ is a direct bond, $C_1$-$C_4$alkyl-CH or $CF_3$—CH, and
Y is phenyl, naphthyl, fluorenyl or anthryl, each unsubstituted or substituted by $C_1$-$C_{12}$alkyl, $C_1$-$C_{12}$alkoxy, halogen, —CN or —$NO_2$.

2. A compound according to claim 1, wherein $R_1$ is methyl or ethyl.

3. A compound according to claim 1, wherein $R_2$ is methyl.

4. A compound according to claim 1, wherein a is 0 or 1.

5. A compound according to claim 1, wherein $R_3$ is unsubstituted or OH-substituted $C_2$-$C_6$alkylene or is phenylene.

6. A compound according to claim 5, wherein $R_3$ is unsubstituted or OH-substituted $C_3$-$C_4$alkylene or is 1,3- or 1,4-phenylene.

7. A compound according to claim 1, wherein $R_4$ is ethylidene, 1,1-propylidene or 1,1,1-trifluoroethylidene.

8. A compound according to claim 1, wherein Y is phenyl or naphthyl, each unsubstituted or substituted by $C_1$-$C_4$alkyl, $C_1$-$C_4$alkoxy, —F, —Cl, —Br, —CN or —$NO_2$.

9. A compound according to claim 1, wherein $R_4$ is a direct bond and Y is 3,5-dinitrophenl-1-yl or 3,5-dicyanophen-1-yl.

10. A compound according to claim 1, wherein $R_4$ is ethylidene and Y is unsubstituted or substituted naphthyl.

11. A compound according to claim 10, wherein —$R_4$—Y is the (R)- or (S)-form of $$\overset{CH_3}{\underset{\bullet}{-CH\text{-naphthyl}}}$$

12. A compound according to claim 1, wherein $R_5$ is the divalent radical of a lactone containing a total of 4 or 5 ring members.

13. A compound according to claim 1, wherein $R_5$ is linear $C_2$-$C_5$alkylene or $C_3$-$C_5$alkenylene each of which is substituted by $C_1$-$C_6$alkyl, $C_1$-$C_6$alkoxy, $C_1$-$C_6$alkylthio, $C_1$-$C_{12}$alkylamino, $C_5$ or $C_6$cycloalkyl, $C_5$ or $C_6$cycloalkoxy, $C_6$-$C_{10}$aryl, $C_6$-$C_{10}$aryloxy, $C_7$-$C_{11}$aralkyl, $C_7$-$C_{12}$aralkoxy, $C_1$-$C_6$haloalkyl, $C_1$-$C_6$hydroxyalkyl, $C_1$-$C_6$alkoxymethyl, ($C_6$-$C_{12}$aryloxy)methyl, ($C_6$-$C_{18}$aryl)methoxymethyl, $C_1$-$C_{12}$acyloxy, —CO—$R_8$, —F, —Cl, —Br, —OH or —CN, where $R_8$ is $C_1$-$C_6$alkyl, cyclohexyl, phenyl or benzyl.

14. A compound according to claim 1, wherein $R_5$ is a radical of formula II

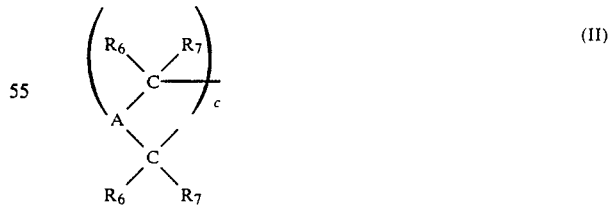

wherein
A is 1,2-phenylene or 2,3-naphthylene, each unsubstituted or substituted by —F, —Cl, —Br, —OH, —CN, —$NO_2$, $C_1$-$C_4$alkyl or $C_1$-$C_6$alkoxy,
c is 0 or 1, and
$R_6$ and $R_7$ are different from each other and are H, $C_1$-$C_6$alkyl, —$CF_3$, unsubstituted phenyl or naphthyl, or phenyl or naphthyl each substituted by —F, —Cl, —Br, —OH, —CN, —NO$_2$, —CF$_3$, C$_1$-C$_6$alkyl or C$_1$-C$_6$alkoxy.

15. A compound according to claim 1, wherein a chiral carbon atom in the radical R$_5$ is α- or β-oriented to the —O—group.

16. A compound according to claim 1, wherein R$_5$ is the R-or S-form of

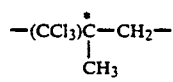

or

17. A compound according to claim 1, which is a stereoisomer of formula

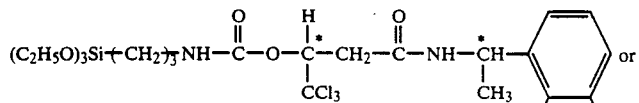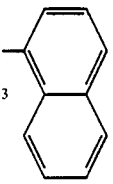 or

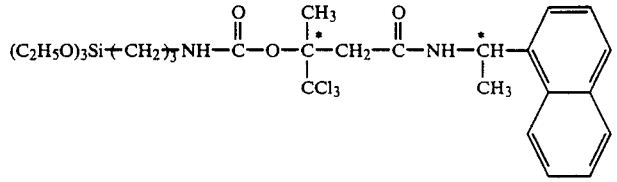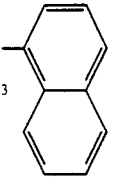

wherein * denotes the chiral carbon atom in R- or S-form.

18. A process for the preparation of a compound of formula I, which comprises reacting a compound of formula III $$(R_1O)_{3-a}Si(R_2)_a-R_3-NCO \qquad (III)$$

with a compound of formula IV

in which formulae above R$_1$, R$_2$, R$_3$, R$_4$, R$_5$, Y and are as defined in claim 1.

* * * * *